(12) United States Patent
Gaskin

(10) Patent No.: US 7,442,847 B2
(45) Date of Patent: Oct. 28, 2008

(54) REMOVING DIAMONDOID COMPONENTS FROM NATURAL GAS AT REDUCED TEMPERATURES

(75) Inventor: Thomas K. Gaskin, Spring, TX (US)

(73) Assignee: Advanced Extraction Technologies, Inc., Houston, TX (US)

( * ) Notice: Subject to any disclaimer, the term of this patent is extended or adjusted under 35 U.S.C. 154(b) by 415 days.

(21) Appl. No.: 11/210,144

(22) Filed: Aug. 23, 2005

(65) Prior Publication Data

US 2006/0111602 A1 May 25, 2006

Related U.S. Application Data

(60) Provisional application No. 60/603,933, filed on Aug. 24, 2004.

(51) Int. Cl.
C07C 7/11 (2006.01)
C07C 7/00 (2006.01)

(52) U.S. Cl. .................................. 585/864; 585/867

(58) Field of Classification Search .................. 585/800, 585/802, 803, 833, 864, 867
See application file for complete search history.

(56) References Cited

U.S. PATENT DOCUMENTS

| | | | | |
|---|---|---|---|---|
| 4,952,747 A | | 8/1990 | Alexander et al. | 585/803 |
| 4,952,748 A | * | 8/1990 | Alexander et al. | 585/803 |
| 4,952,749 A | | 8/1990 | Alexander et al. | 585/803 |
| 4,982,049 A | | 1/1991 | Alexander et al. | 585/803 |
| 5,019,665 A | | 5/1991 | Partridge et al. | 585/803 |
| 5,120,899 A | * | 6/1992 | Chen et al. | 585/803 |
| H1185 H | | 5/1993 | Henderson et al. | 423/245.2 |
| 5,245,104 A | | 9/1993 | Cullick | 585/812 |
| 5,461,184 A | | 10/1995 | Swanson | 585/803 |

OTHER PUBLICATIONS

K.E. Woodcock & M. Gottlieb, Natural Gas in: Kirk-Othmer Encyclopedia of Chemical Technology (2004 ed.), vol. 12, 365-386.*
A. S. Cullick et al. "An Analysis of Solid-Forming Characteristics from a Produced Gas Stream," *Proceedings of the Seventy-Third GPA Annual Convention*, New Orleans, Louisiana Mar. 7-9, 1994, U.S.A., pp. 22-28.

* cited by examiner

*Primary Examiner*—Glenn Caldarola
*Assistant Examiner*—Randy Boyer
(74) *Attorney, Agent, or Firm*—Howrey LLP

(57) ABSTRACT

A process for separating diamondoids and water from a gas stream that is being cooled to below atmospheric temperature is disclosed. The multi-component gas stream is contacted with a diamondoid solvent and a water solvent (glycol) simultaneously. The feed gas can be cooled to temperatures of at least −40° F. without formation of water-based or diamondoid solids. Downstream equipment is protected from large accumulations of diamondoid solids or liquids. The feed gas may be natural gas, coal seam gas, associated gas, or other naturally occurring gases. The rich solvent with diamonoids may be regenerated or simply recirculated with make-up of fresh solvent and a purge of rich solvent. The rich glycol and rich diamondoid solvent streams are each separated from the feed gas after cooling. The lean glycol and lean solvent can be mixed using static mixers in order to inject with a single set of nozzles.

19 Claims, 4 Drawing Sheets

REMOVING DIAMONDOID COMPONENTS FROM NATURAL GAS AT REDUCED TEMPERATURES

The present application claims benefit of priority to U.S. provisional application Ser. No. 60/603,933 filed Aug. 24, 2004, the entire contents of which are incorporated by reference herein.

FIELD OF THE INVENTION

The invention relates to the field of chemical processing and, more specifically, to the processing of hydrocarbon gas streams. In particular, a method and apparatus for separating the adamantine and heavier diamondoid components from a hydrocarbon gas stream is disclosed.

BACKGROUND OF THE INVENTION

Naturally occurring hydrocarbon gases such as natural gas, coal seam gas, gas associated with crude oil or other hydrocarbon deposits are often contaminated with one or more undesired components. These undesired components may have to be removed to make the gas marketable. Contaminants may include, but are not limited to, acid gases such as carbon dioxide and hydrogen sulfide, water, oxygen, nitrogen, and larger than desired amounts of hydrocarbons heavier than methane. Any or all contaminants may need to be at least partially removed to make the gas marketable. Pipeline transportation systems typically impose specifications as to the amount of water, acid gases, oxygen, and heavier hydrocarbons are allowed in the pipeline system. Heavy hydrocarbons may be limited by the dew point temperature of the gas, or by the heating value of the gas.

A less common contaminant of these gases, particularly of some natural gas, is a family of caged hydrocarbons referred to as diamondoids. This family of high boiling point, saturated, poly-cyclic compounds includes adamantine, diamantane, triamantane, and heavier compounds. These components are characterized by high melting points and high vapor pressure in natural gases. When a gas containing diamondoids is reduced in pressure, temperature, or both, a portion of the diamondoid components can condense and solidify after saturation in the gas is reached. Condensation and solidification can cause fouling and plugging of the gas-handling equipment, a potentially dangerous condition. One reference for physical property measurements and predictions of diamondoid behavior is published in the "Proceedings of the seventy-third GPA annual convention", Mar. 7-9 1994, as a paper titled "An analysis of solid-forming characteristics from a produced gas stream" by A. S. Cullick et. al. This reference includes data for solubility of diamondoids in gas at various pressures and temperatures along with melting points and relative volatility (k-value) data and prediction methods.

U.S. Pat. Nos. 4,952,747; 4,952,748; 4,952,749; 5,019,665; H1,185; and U.S. Pat. No. 5,461,184 explore and describe systems for removal of diamondoid components from gas systems, particularly removal from natural gas utilizing one or more solvents and also utilizing silica gel. In a typical system, a suitable liquid solvent with capacity to maintain diamondoids in liquid solution is injected into the gas handling system at a point upstream of where the diamondoids would form solids due to lowering of pressure or temperature. Injection points can include into a natural gas production well tubing, into a production well pipe upstream of any choke valves, and upstream of any production coolers. The solvent, containing absorbed diamondoids, is typically separated from the gas and then recirculated using a pump until it becomes saturated with diamondoids and must be replaced. Continuous regeneration of the solvent and removal and concentration of the diamondoids is also described. Regeneration using a standard refluxed and reboiled distillation tower is described, along with azeotropic distillations. The gas stream may also be contacted countercurrently with the solvent in a mass transfer operation such as a packed or trayed tower. Regeneration may also be used in this type of application. If a solvent is injected into a gas stream and flows con-currently with the gas, the solvent inhibits the formation of solids by allowing the diamondoid compounds to enter solution. At the point where the solvent is removed from the system a single equilibrium stage between the vapor and liquid has been achieved, at the final physical conditions. Appropriate solvents can hold 10% volume or more diamondoids in solution. When the solvent is not regenerated, circulation, make-up, and purge rates are set so as to control the amount of diamondoids in the solvent. When a mass transfer tower is used, a stagewise operation occurs, and the amount of diamondoids absorbed into the solvent is set by operating condition temperature and pressure, number of stages allowed, amount of diamonoids in the lean solvent, and so on. Silica gel is described as a polishing step for additional removal.

Solvents used for maintaining condensed diamondoids in solution typically contain aromatic compounds. Diesel is the most common solvent recommended. Kerosene, aromatics, mixed xylenes, and others are also mentioned. Other liquid hydrocarbons can also keep the condensed diamondoids from dropping out of solution and fouling the systems. In fact, when heavier hydrocarbons are present in the naturally occurring gas, diamondoids may not be noticed, even if they are present, as a portion of the of the heavier hydrocarbons will condense and form a liquid phase that can keep the diamondoids from solidifying, and form this liquid phase under conditions that are similar to those that cause the diamondoids to condense—such as when temperature or pressure is lowered. In this manner, the naturally occurring hydrocarbons act as a diamondoid solid inhibitor, just as injection of diesel into a hydrocarbon dry system can. In the case of condensing naturally occurring heavy hydrocarbons, the potential issue of distribution of the liquid is not a problem as it forms directly from the gas, however, distribution of an injected solvent can be a problem.

Acid gases are typically removed from hydrocarbon gases using chemical solvents such a amines, including MEA, DEA, DIPA and MDEA in a solution with water. Physical solvents may also be used. The hydrocarbon gas is often saturated with water after these processes, and may need to be removed.

Water is common is produced hydrocarbon gases. Removal of water is often required to meet pipeline specifications. Removal of water may also be required to allow for low temperature processing of the gas without hydrate formation for heavier hydrocarbon removal from the gas.

A typical pipeline specification is 7 lbs. water per MMscf of gas. This specification is easily reached with a variety of common methods. Perhaps the most common is to use a TEG solvent (tri-ethylene glycol) in a counter-current mass transfer contacting tower utilizing trays of packing. The lean TEG absorbs the water at atmospheric temperatures in the contactor, and the resulting water-rich TEG is regenerated in a second tower, with the water rejected as the overhead vapor product and the lean TEG removed as the bottoms product. This is a very common and proven method of dehydration. TEG systems are commonly installed on processed gases after initial liquid hydrocarbon and produced liquid water separation. They are also installed downstream of acid gas removal systems. TEG is a stagewise mass transfers absorption system, just as a trayed diamondoid system can be. A typical TEG system with about 99% weight TEG purity will achieve approximately 100° F. dew point depression, dependent on contactor temperature.

Dehydration of gases to lower water content may be necessary when removal of heavier hydrocarbons is desired. Hydrocarbon removal systems to meet dewpoint or BTU specification for the gas, or to enable marketing of the recovered liquid as a separate stream typically involves reducing the temperature of the gas to below atmospheric temperature. Dehydration to lower water content can be achieved with several technologies, all well proven, including use of molecular sieves (adsorption of water), membrane systems, and enhanced TEG systems that result in leaner lean solvent water concentration (enhancing the equilibrium for water absorption at the top stage of the tower), all of which may operate at atmospheric temperature. Ethylene glycol (EG) and methanol systems are common inhibition methods employed as the gas is cooled. If the gas has not been dehydrated, water will condense when the gas is cooled, and under certain conditions, typically at below 70 deg. F., methane and other hydrocarbons can form hydrate molecules that will solidify in the system. Ice will form at temperatures below 32° F. The EG or methanol will hold condensed water in solution, without allowing it to freeze or form hydrates, as long as certain well-established compositional conditions are met. Conditions include that the EG or methanol are present at the point where the water condenses, and that the solution containing water does not contain so much water that a concentration that can freeze occurs. EG is typically injected into the system with one or more spray nozzles located upstream of points where the gas is cooled by heat exchange or by auto-refrigeration associated with pressure drop. The gas containing water is typically routed through the tube-side passes of shell and tube heat exchangers in order to keep the EG in contact with the gas as it cools. Tubes can be cut off flush with the exchanger tube-sheet to allow sprayed EG to enter each tube, rather than having EG that does not directly enter a tube when sprayed to simply flow down the surface of the exchanger tube-sheet and then flow only through the bottom several tubes. Several times the theoretically required volume of EG is typically circulated, to allow for poor distribution into the tubes. One or more spray nozzles are typically used to ensure coverage of the tube-sheet. Use of EG and methanol systems are well documented in literature, and proven. A typical lean EG stream is 80% weight EG, 20% weight water. The water rejected from the rich EG during regeneration may be vented to atmosphere, or may be routed to a VOC recovery system or flare if co-aborbed hydrocarbons present a VOC, flammability, or personnel exposure hazard. EG does have a documented affinity for absorbing aromatics.

Hydrocarbon liquids may be recovered by simply reducing the temperature of the gas with a refrigeration system, and separating the condensed hydrocarbon liquid. In this simple system, EG hydrate inhibition is often employed. EG is sprayed into the gas at points where the gas is cooled, such as when the gas enters heat exchangers. The rich EG, containing water, can be separated in a separate compartment of the same separator used for separation of the condensed liquid hydrocarbon. Liquid hydrocarbon is recovered, gas hydrocarbon dewpoint is met, and the gas is dehydrated in a very simple system. This type of system is often referred to as a "low temperature separator" system, or "LTS". Diamondoids would not typically be a problem is this type of system, as the condensing hydrocarbon components may well keep any condensing diamondoid compounds in solution.

Hydrocarbons heavier than methane are also recovered using "cryogenic" technologies, including turbo-expander plants, JT plants, and low temperature refrigeration plants. These plants are characterized as operating below the temperatures of simple LTS systems or of refrigerated absorption systems that have a typical minimum process temperature of greater than minus 40° F. Cryogenic plants are also characterized by achieving liquid hydrocarbon recovery without the use of a circulating solvent for absorption—the gas is cooled to the extent that all of the desired product can be condensed as a liquid. Water dehydration for these systems must achieve water dewpoint temperatures suitable for the minimum process temperature, typically in the range of minus 100 to −150° F. This can be achieved using molecular sieves for adsorption of water, followed by regeneration of the adsorbed water using lower pressure and/or higher temperature. Methanol may also be used, but is less common. Molecular sieve systems could be used for simple LTS or solvent absorption systems for liquid recovery, but are typically not used due to cost relative to simple EG injection inhibition systems.

Nitrogen contamination can also be removed using either absorption technology or cryogenic technology. As with liquid hydrocarbon recovery, the cryogenic processes typically use molecular sieves for dehydration upstream of the nitrogen rejection plant, and absorption systems typically use EG injection for hydrate inhibition and water removal. The absorption system for nitrogen rejection can also use molecular sieves, methanol injection, membranes, enhanced TEG systems, or others for dehydration. The absorption systems operate at warmer temperatures, typically above −40° F., and therefore EG injection is adequate and is typically employed as the most economical method for water removal/hydrate inhibition.

Absorption using a physical solvent to remove the heavier components and therefore separate them from the light components, a process known as the Mehra Process™, can be employed. The Mehra Process is described in several U.S. Patents, including U.S. Pat. Nos. 4,623,371, 4,832,718, 4,833,514, and 5,551,972. These patents describe systems for absorption/flash regeneration systems for removal of light components such as nitrogen or hydrogen from heavier components such as methane or ethylene. They address systems wherein the physical solvent used is external, meaning a made up of component(s) added to the system, and also systems wherein the physical solvent used is internally generated and is therefore composed of heavier component(s) in the feed gas. An improvement to these processes is also described in U.S. Pat. No. 6,698,237 by Thomas K. Gaskin, which addresses use of stripping gas to enhance the performance of flash regeneration systems. A further improvement is described in U.S. patent application Ser. No. 11/076,356 (incorporated herein in its entirety by reference) by Thomas K. Gaskin, which describes the use of a cryogenic temperatures in processing gases in solvent absorption systems, and in provisional U.S. patent application 60/603,933 filed Aug. 24, 2004 (incorporated herein in its entirety by reference), also by Thomas K. Gaskin. In this process, the heavier components are absorbed away from the light component(s) using a circulating physical solvent. Reducing the pressure of the rich solvent in a flash separator releases the heavier component and regenerates the solvent for recirculation to the absorber. The physical solvent may be a liquid chosen for its physical properties, one property being that it is heavier than the component to be absorbed from the light component. The physical solvent may also be made up entirely of the heaviest components of the feed gas stream. These heaviest components are those that do not readily vaporize in the flash regeneration of the circulating solvent. These absorption processes are characterized in that a feed stream comprising multiple components enters the process and two or more streams, each being enriched in at least one of the components, leaves the process.

Gas reserves that do not contain recoverable hydrocarbon liquids may have a greater tendency for containing diamondoids. It may also be that diamondoids that are present in gas streams with recoverable liquid hydrocarbons are simply not noticed or analyzed to determine diamondoid content, simply because the diamondoids do not present a problem. What this means is that a typical natural gas stream that could contain diamondoids would not typically have a low temperature liquid recovery plant associated with it, and development of systems to both dehydrate the feed gas and allow for diamondoid removal to the extent required for low temperature operation has not received much attention.

Development of gas reserves containing nitrogen has not been accomplished at nearly the same pace as development of reserves that do not contain nitrogen. Removal of nitrogen adds another cost to development of reserves, and has therefore been avoided to a large extent. Development of gas reserves that contain nitrogen that must be removed, that are also very low in hydrocarbon content heavier than methane and therefore would not have a hydrocarbon liquid recovery technology installed, and that are known to contain diamondoids in the raw gas is exceptionally rare.

Removal of water, diamondoids, and nitrogen from a naturally occurring gas stream has not been required historically. Development of the solvent absorption nitrogen rejection process operating in a temperature range of 0 to −40° F., along with applications to the rare gas that contains diamondoids and no recoverable liquid hydrocarbons, has led to the need for such a process. Any process that can improve the ability to remove diamondoids and water from the feed of a low temperature process would be appreciated as a technical contribution to the art.

BRIEF SUMMARY OF THE INVENTION

One aspect of the present invention is a process for separating water and diamondoids from the feed gas entering a gas processing facility operating at 0 to −40 degrees F. In one aspect of the invention, the gas processing facility is an absorption/flash regeneration nitrogen rejection process. Water and diamondoids can both be removed when the gas is chilled to the reduced process temperature. Ethylene glycol is injected to prevent freezing and hydrate formation when the gas is chilled, the condensing water enters solution with the glycol and is removed with the glycol after separation at low temperature. Kerosene, diesel, or other suitable solvent is injected into the feed gas, and prevents deposition of diamondoid solids as the gas is chilled, as the diamondoids enter solution with the solvent. These two processes can operate in the presence of each other when properly introduced into the feed gas cooling equipment. Use of a static mixer to combine the circulating lean ethylene glycol with the circulating lean kerosene solvent upstream of a spray nozzle(s) allows distribution of both liquids without interference with each other, achieving adequate distribution of both into the gas stream to prevent deposition of either water based compounds or diamondoids.

BRIEF DESCRIPTION OF THE DRAWINGS

FIG. 5 shows a process according to the present invention wherein water and diamondoids are removed simultaneously as the feed gas to a processing plant is chilled.

DESCRIPTION OF PREFERRED EMBODIMENTS

Figure 1:
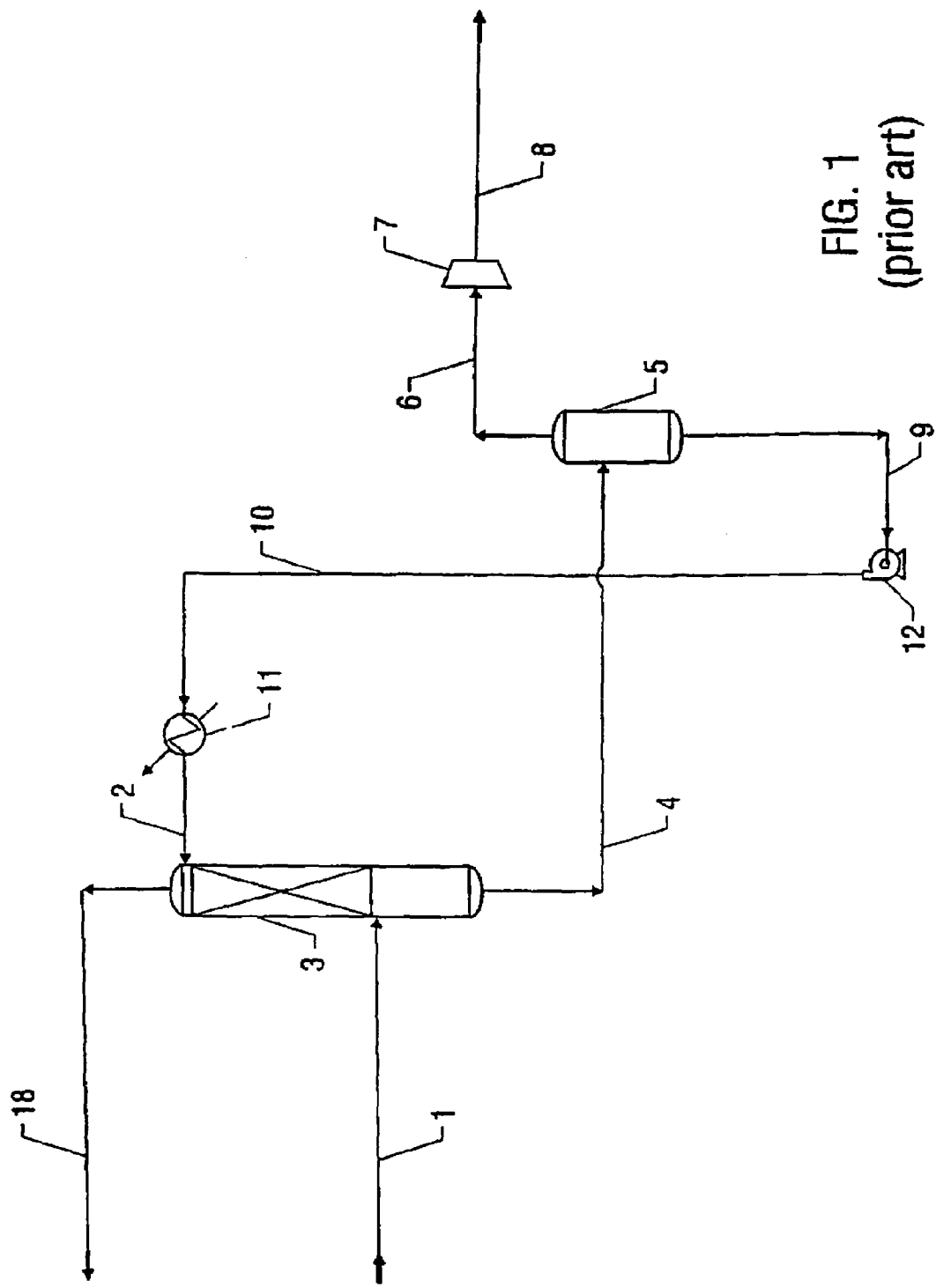
FIG. 1 shows a prior art process for separating the components of a gas stream.

It should be understood that pipelines are in fact being designated when streams are identified hereinafter and that streams are intended, if not stated, when materials are mentioned. Moreover, flow control valves, temperature regulator devices, pumps, compressors, and the like are understood as installed and operating in conventional relationships to the major items of equipment which are shown in the drawings and discussed hereinafter with reference to the continuously operating process of this invention. All of these valves, devices, pumps, and compressors, as well as heat exchangers, accumulators, condensers and the like, are included in the term "auxiliary equipment". The term "absorber" is employed for a gas/solvent absorbing apparatus, and refers to any apparatus known in the art in which a gas is contacted with a solvent to absorb part of the gas into the solvent. According to certain embodiments, an absorber may include internals such as plates, packing, baffles and the like, to promote mass transfer.

Several processes for removal of contaminants from natural gas include chilling of the feed gas to sub-atmospheric temperatures. When propane refrigeration is used for chilling, the gas may be chilled to approximately −40° F. minimum temperature. Processes that employ this type of chilling include low temperature separators, or "LTS's" for removal of hydrocarbons heavier than methane as a liquid product, solvent absorption processes for removal of hydrocarbons heavier than methane to a greater extent than possible with a simple LTS, and nitrogen rejection plants that employ a circulating solvent for absorption of methane away from the unabsorbed component nitrogen. In the gas a nitrogen rejection plants, or "NRU's", the methane absorbed in the circulating solvent is typically released from the solvent by reducing the pressure of the rich solvent, thereby creating the separated vapor methane product and also recreating the lean solvent after release of the methane.

Water is a common gas contaminant. Water may be removed by a variety of processes. Processes for removal of contaminants that utilize reduced temperatures must have water present in the feed gas removed to prevent hydrate formation in the process. In processes that operate at reduced temperature, injection of ethylene glycol is frequently used to prevent hydrate or ice formation by allowing the condensed water to enter a solution with glycol, thereby preventing formation of ice or hydrates of water with methane or heavier components of the gas. The liquid solution of water and glycol is separated from the gas, regenerated using heat for rejection of water from the glycol, and then the lean glycol is recirculated to the feed gas.

Diamondoids are a much rarer contaminant of gases. Diamondoids may also be removed by injection of a lean solvent. Presence of the solvent as the gas is cooled allows the diamondoids to enter solution rather than for solids.

In one aspect of the present invention, water and diamondoids are removed simultaneously from a gas stream during cooling to a temperature greater than −40° F. by injection of ethylene glycol and a hydrocarbon solvent. The ethylene glycol allows the condensing water to enter solution without forming solids. The hydrocarbon solvent allows the condensing diamondoids to enter solution without forming solids. The ethylene glycol and hydrocarbon solvent are inhibitors, preventing the formation of solids in the gas processing system as the gas is cooled. In another aspect of the present invention, the rich glycol phase containing water and glycol is separated from the chilled gas in a separator vessel. In another aspect of the present invention, the hydrocarbon solvent with diamondoids is also separated in a separator vessel. The separated glycol and hydrocarbon solvent solutions may be regenerated for re-use, or circulated until a maximum amount of contaminant is reached. A continuous make-up of fresh solvent and blowdown of rich solvent may also be used to control the amount of contaminant in the solvent.

In one aspect of the present invention, the hydrocarbon solvent used is diesel. In another aspect, the solvent is kerosene. Kerosene can be used at lower temperatures than diesel without solidifying or "gelling". In another aspect, the solvent is diesel with components added to prevent gelling. In another aspect, the solvent used is an aromatic compound with an affinity for holding diamondoids in solution, such as any pure aromatic compound, any mixture of aromatics, or any mixture of hydrocarbons that contains some portion of aromatic compounds, or any hydrocarbon that will allow condensation of the diamondoids without formation of solids. Use of natural gas liquid hydrocarbons as the solvent is also possible, but a much larger amount of liquid would be required due to low ability to hold diamondoids in solution and high vaporization losses in the process.

Ethylene glycol is typically sprayed into the gas prior to a stage of cooling, such as a heat exchanger, with the gas containing water on the tube side of the exchanger, and the glycol being sprayed so as to enter all tubes with the gas. Glycol is sprayed upstream of each heat exchanger, valve, or other temperature reduction system to ensure adequate distribution of glycol. If a plate-fin exchanger is used, glycol is injected into each individual gas passage in the plate fin exchanger. In one aspect of the present invention, the diamondoid solvent is injected at the same locations and in the same manner as is typically accomplished with ethylene glycol. In another aspect of the present invention, the rich solvent and rich glycol are each regenerated in distillation towers. In another aspect of the present invention, the diamondoid solvent is injected during an initial cooling stage operating at a temperature above the water hydrate formation temperature, and the rich solvent may be separated prior to further cooling, and both the diamondoid solvent and the glycol are injected when the gas is cooled below the hydrate formation temperature of about 70° F. In a further aspect of the present invention, either or both of the rich streams are heated prior to pressure reduction to ensure that any components in either stream do not solidify due to the pressure reduction auto-refrigeration effect added on to the already reduced operating temperature.

In another aspect of the present invention the lean ethylene glycol and lean hydrocarbon solvent streams are injected into the gas using the same spray nozzle(s). In this manner, each lean stream may be injected without interference from separate spray nozzles distributing separate liquids into the gas. In another aspect, the glycol and solvent are mixed upstream of the spray nozzle using a static mixer, or other device which can promote missing such as a valve or an orifice, to ensure a nearly homogenous mixture enters the spray nozzle(s) continuously and therefore distributes consistent amounts of each liquid uniformly into the gas.

In a further aspect of the present invention, the solvent system for diamondoid solid formation inhibition is added to an existing glycol spray system in order to inhibit the formation of diamondoid solids that were not planned for in the original facility design. This would be a retrofit of an existing glycol system to accommodate a new or unexpected contaminant consisting of diamondoids.

In another aspect of the present invention, the gas is substantially dehydrated upstream of the gas cooling, and only solvent injection for diamondoid inhibition is required. In another aspect, some diamondoid removal is accomplished prior to entering the facility, and the solvent system with spray nozzles is installed as a supplemental system to further guard against solid formation, or to allow operation at the reduced temperature. In another aspect of then present invention, diamondoid inhibition and separation is required so as to allow such small amounts of diamondoids to remain in the gas that further cryogenic processing is possible, such a liquefaction of the entire gas stream for transport, or removal of ethane from a methane stream.

FIG. 1 shows a prior art process suitable for separating nitrogen from methane, or other separation of a light gaseous component from a heavier gaseous component. According to the process of FIG. 1, hydrocarbon feed gas 1 is counter-currently contacted with lean solvent 2 in absorber 3, generating an overhead stream 18 and a rich solvent bottoms stream 4. The rich solvent bottoms stream 4 can is directed to one or more flash separators 5. The number of separators can vary. According to one embodiment, there is a single flash separator 5. The component absorbed in the solvent is released in separator 5, and is separated as vapor stream 6. While only one flash stage is depicted in FIG. 1, multiple separators could be used. The pressure of stream 6 is elevated via compressor 7, yielding stream 8 as a product stream of the process. The regenerated lean solvent leaves separator 5 as a liquid stream 9 and is returned to absorber 3 as stream 10 via pump 12. Lean solvent stream 10 may be cooled in solvent cooler 11 prior to re-entering the extractor 3. If the multi-component gas stream 1 entering the process of FIG. 1 comprises methane and nitrogen, for example, natural gas contaminated with nitrogen, then an external solvent would be utilized and stream 18 will be enriched with nitrogen and stream 8 will be enriched with methane.

Figure 2:
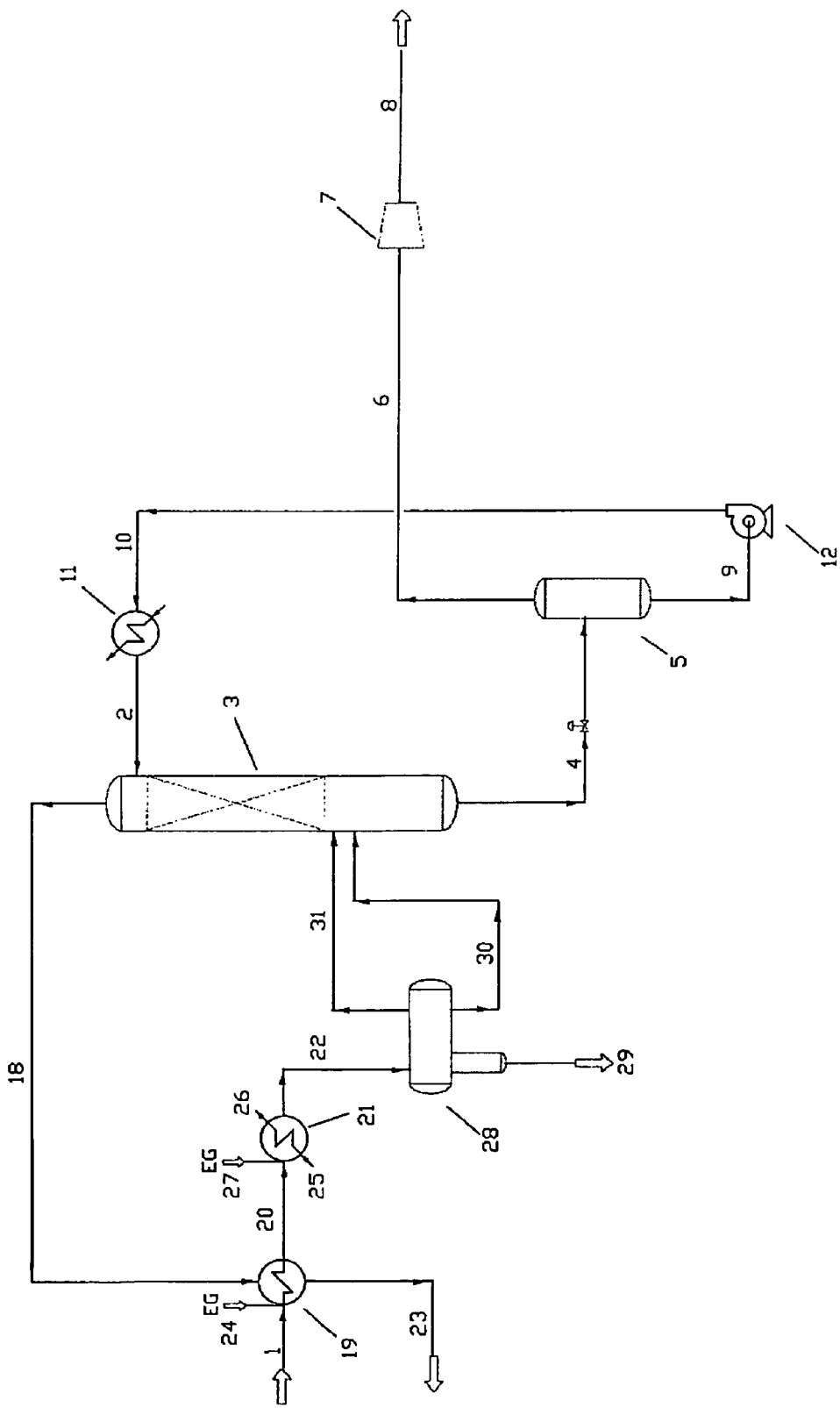
FIG. 2 shows a prior art process for separating the components of a gas wherein the process includes chilling of the inlet gas and ethylene glycol injection for hydrate inhibition.

FIG. 2 shows a prior art process similar to FIG. 1 with the addition of inlet gas heat exchange and chilling in order to operate the facility at a reduced temperature. It is assumed that the gas feed in FIG. 2 contains water and that ethylene glycol injection will be required to prevent water freezing and or hydrate formation. Gas feed stream 1 is cooled in heat exchanger 19 to become cooled stream 20. Cooling is provided by light component gas stream 18, which is reheated to become stream 23. Lean ethylene glycol stream 23 is injected (sprayed) at the entrance of the heat exchanger 19 to allow distribution of the liquid into each of the heat exchanger tubes included in exchanger 19. Cooled gas stream 20 is further cooled in exchanger 21, using a refrigerant for this additional cooling, and leaves as colder stream 22. Using propane as the refrigerant, the temperature of stream 22 is typically between 0 and −40° F. The refrigerant enters the shell side of then exchanger as stream 25, and leaves as stream 26. The ethylene glycol added in exchanger 19 may mostly settle into the bottom tubes of exchanger 21 and not provide adequate contact of glycol with the feed gas to prevent freezing or hydrate formation as the gas is further cooled and additional free liquid water forms. Additional lean glycol is sprayed at the entrance of exchanger 21, indicated by stream 27. The chilled gas stream 22 contains feed gas, rich glycol containing water in solution, and any hydrocarbons that condensed as a separate liquid phase during the cooling operations. Stream 22 enters separator 28, where the phases are separated. Rich ethylene glycol is the heaviest stream, and is separated from the bottom of vessel as stream 29. Any liquid hydrocarbon floats on top of the glycol, and can be separated either after an internal weir or from the bottom of the vessel if the glycol is separated in a boot (as is shown in FIG. 2), and leaves the separator as stream 30. Separated gas leaves the separator as stream 31. The rich ethylene glycol is typically regenerated by having the water removed, and is recycled back to the exchangers. The feed gas stream 31 and condensed liquid stream 30 are routed to the absorber 3. The remaining equipment, streams and process in FIG. 2 are as described for FIG. 1.

Figure 3:
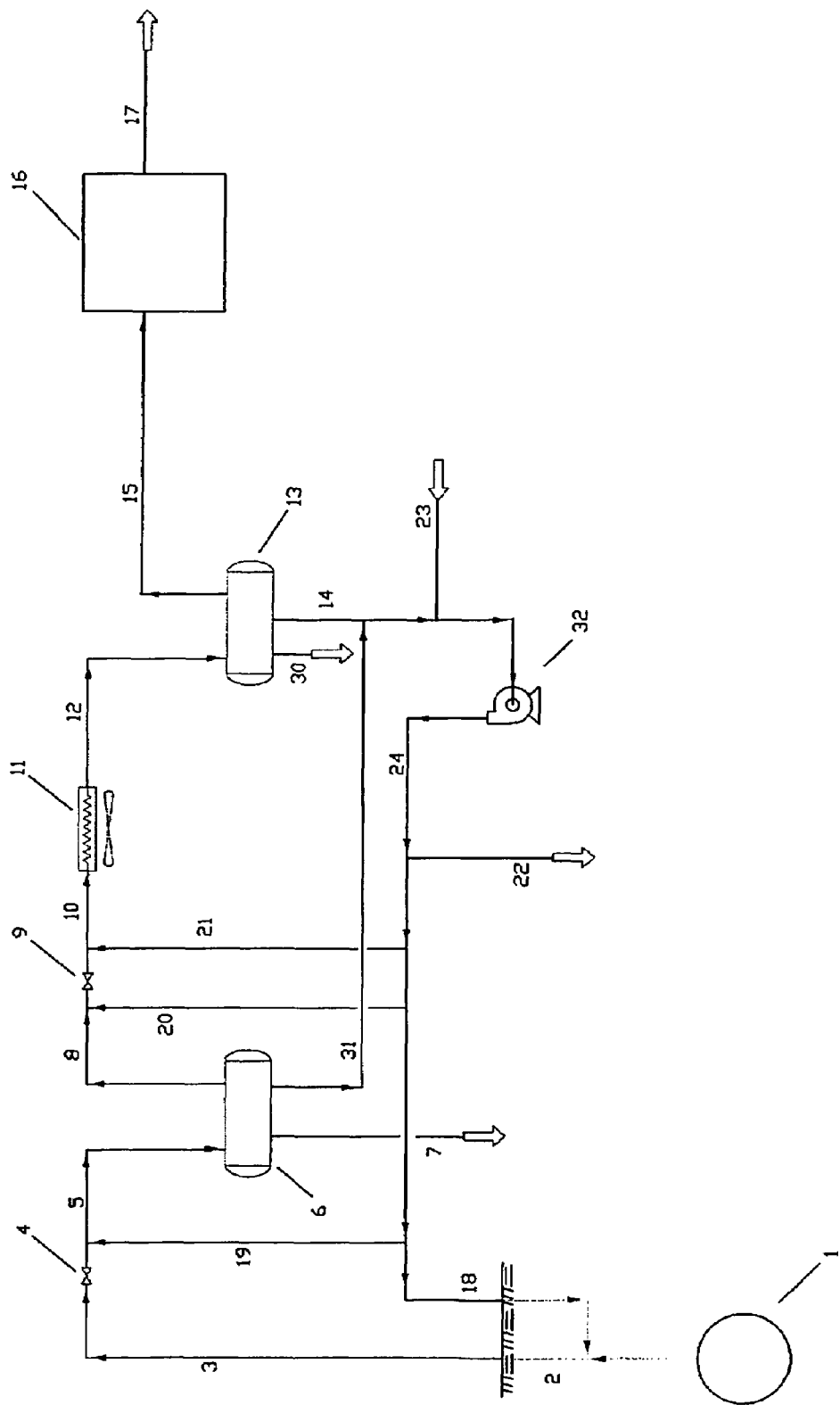
FIG. 3 shows a prior art process for injection and recirculation of a solvent to prevent diamondoid deposition in natural gas production equipment.

FIG. 3 describes prior art for injection of a solvent to prevent diamondoid deposition in a natural gas production well and surface facilities. Natural gas from reservoir 1 is produced through well pipe 2 and reaches the ground surface as stream 3. Pressure is reduced through choke 4. Reduced pressure stream 5 flows into production separator 6, with free water and or hydrocarbons leaving as stream 7. Gas leaves as stream 8, and additional pressure drop may be taken across valve 9, with the gas exiting the valve as stream 10. The gas is cooled in cooler 11, exiting as stream 12, and is routed to separator 13, where any additional water and or hydrocarbon that has been condensed may be separated and leave the system as stream 30. Gas stream 15 is then routed to any additional treatment and/or separation required in order to meet pipeline specifications for transport using the equipment represented by block 16, with the on-specification gas exiting as stream 17. Block 16 will typically include a water removal facility such as a TEG contactor as a minimum. If the produced gas from the reservoir does not contain any hydrocarbons heavier than methane, or very little, there will be no liquid hydrocarbon condensation in the indicated production facilities. Separator liquid streams 7 and 30 will contain only condensed liquid water, or free water that was in the well and was produced along with the gas. If there are diamondoids present in the produced gas from the reservoir, and very little other hydrocarbon content heavier than methane, then a portion of the diamoidoids in the gas will condense and can solidify and foul the equipment indicated in FIG. 3. Any point in the production where temperature or pressure is reduced may lead to diamondoid separation and fouling. A suitable solvent can be used to take any condensing diamondoids into solution. In FIG. 3 a lean solvent is injected into the well pipe as stream 18, into the produced gas pipe as stream 19, upstream of the second valve as stream 20, and downstream of this valve and upstream of the cooler as stream 21. These and other points of injection will ensure that a solvent is available at all possible condensation points to prevent diamondoid deposition. The diamondoid-rich solvent can be separated as a separate phase as streams 31 and 14 from the separators 6 and 13. The rich solvent may be recirculated using pump 32, with the resulting higher pressure stream 24 being redistributed to the injection points. The diamondoid concentration in the solvent can be controlled by removal of part of the solvent as stream 22, and addition of fresh solvent as stream 23. Rich diamondoid containing solvent streams 14 and 31 may also be routed to a solvent regeneration system for removal of all or part of the contained diamondoids, and then the lean solvent returned as part of stream 23.

Figure 4:
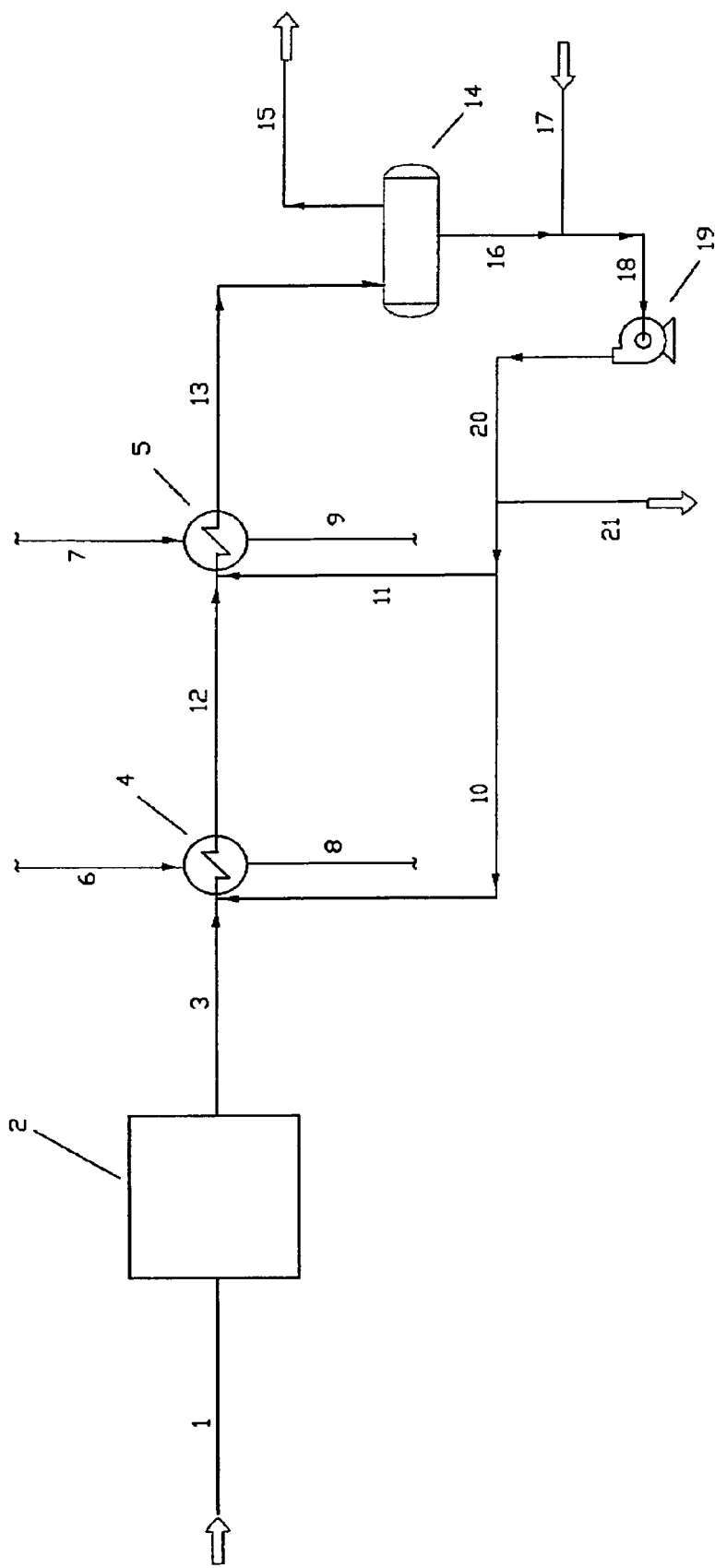
FIG. 4 shows a process according to the present invention for separating diamondoid components from a gas stream being chilled, after the stream has been dehydrated.

FIG. 4 depicts a process of the present invention. Gas stream 1 contains contaminants that are removed by one or more processes in block 2, with the gas leaving as steam 3. Stream 3 is a methane-rich gas that contains only diamondoids and nitrogen as undesired contaminants. In preparation for nitrogen removal, the gas stream is cooled in heat exchangers 4 and 5. Streams 6 and 7 are used to cool the feed gas, with stream 6 often being a cool stream from the nitrogen removal process and stream 7 often being a propane refrigerant stream. The corresponding warmed streams leaving the exchangers are streams 8 and 9. A liquid hydrocarbon solvent is injected into the gas at the entrance to the tubes of exchangers 4 and 5 and is indicated as streams 10 and 11. This solvent captures any condensing diamondoid components into solution with the solvent. The cooled gas, with solvent containing diamondoids is indicated as streams 12 and 13. Stream 13 enters separator 14, where the rich solvent containing diamondoids is separated from the chilled gas. The gas exits as stream 15, and continues to the remainder of the nitrogen rejection process. The separated solvent with diamondoids, stream 16, leaves the bottom of the separator. Stream 16 is combined with any make-up or purified solvent indicated as stream 17, and enters pump 19 as stream 18. Solvent leaves the pump as stream 20 and is routed back to the exchanger injection points as streams 10 and 11. Diamondoid concentration in the solvent is controlled by removal of all or part of the solvent as streams 21 and/or 16. Solvent may be stored, sold, or regenerated. Regenerated solvent can be used as make-up in stream 17. Regeneration equipment, such a distillation towers, are not indicated in FIG. 4. Note that the process of FIG. 4 may also be used to remove nearly all diamondoids from a gas stream by chilling to low temperature in the presence of solvent, thereby allowing further processing at even lower temperatures, including cryogenic temperatures, with much lower diamondoid-fouling potential than if the system of FIG. 4 were not installed.

FIG. 5 depicts a further process of the present invention. As with the process of FIG. 4, a feed gas is pretreated, and then is cooled as part of preparation for another process, such as a nitrogen rejection facility. In FIG. 5, the feed gas stream 1 is pretreated for contaminant removal in block 2, leaving as stream 3. Stream 3 still contains undesirable contaminants of water, diamondoids and as an example, nitrogen. The remaining constituent of the gas is methane with minor amounts, if any, components heavier than methane. Following the same process as in FIG. 4, gas stream 3 is cooled in exchangers 4 and 5 by streams 6 and 7 which leave as streams 8 and 9, with the cooled and chilled gas indicated as streams 12 and 13. Injection upstream of the exchangers is streams 10 and 11. In FIG. 5, the injected streams 10 and 11 are not just the diamondoid solvent. These streams comprise both diamondoid solvent and ethylene glycol. Lean ethylene glycol solution streams 20 and 21 are measured using flow indicators 22 and 23, and lean diamondoid solvent streams 24 and 25, measured by flow indicators 26 and 27, to become combined streams 28 and 29. Streams 28 and 29 contain the desired flow rates of each component stream the glycol and the solvent, but the two streams are not a homogenous mix. Streams 28 and 29 are routed through static mixers 30 and 31 that utilize a combination of pressure drop and stationary mixing vanes to blend the two immiscible liquids into homogenous streams 10 and 11 which as suitable for injection through one or more nozzles to form spray patterns that will ensure that suitable amounts of both the glycol and the solvent enter the tubes of the exchangers to prevent formation of either diamondoid or water solids in the system. Stream 13 contains the chilled feed gas and the rich solvent and rich ethylene glycol. Note that static mixers 30 and 31 can alternatively be valves, orifices, or other devices which can induce mixing of the liquids. Stream 13 enters three-phase separator 14. The rich glycol is the heaviest phase, and is separated and removed as stream 17.

The rich hydrocarbon diamondoid solvent is separated as stream 16. The rich solvent and diamondoid stream may be recycled back to exchangers, or may be partially or fully regenerated prior to recycle. The gas exits as stream 15 and continues for further processing, such as nitrogen removal. Between 10 and 30 minutes residence time is often allowed for separation of glycol/hydrocarbon phases in a cold separator of this type. The rich glycol stream 17 is routed to a regeneration system. As stream 17 may contain minor amounts of diamondoids, FIG. 5 indicates that that stream 17 is first warmed using exchanger 32, with the warm stream leaving as stream 33 and only then having a pressure reduction across valve 34 to become lower pressure stream 35, at a pressure suitable for standard ethylene glycol regeneration processes. Exchanger 32 prevents the pressure drop of valve 34 from auto-refrigerating the stream due to Joule-Thompson effects to a temperature cold enough for diamondoids to solidify in the stream. A similar exchanger may also be installed on the rich solvent stream 16 to prevent the potential for diamondoid fouling at lower pressure. Note also that an absorption tower can be installed on top of or downstream of the separator 14, with gas stream 15 entering the bottom of the absorber and a lean solvent entering the top, accomplishing additional diamondoid removal. The solvents used for diamondoid solids inhibition can also work as absorbents, and inclusion of the tower adds additional stages of equilibrium, allowing lower diamondoid concentrations in the overhead gas. A regenerated or fresh solvent would achieve the lowest diamondoid concentration. Solvent injection upstream is still required, in order to allow the gas to be chilled without diamondoid fouling. An absorption tower can also be installed at a point during the feed gas cooling that is not at the ultimately coldest point. In this case, the absorption using a lean solvent can at times negate the need for injection of the solvent as an inhibitor in the colder feed gas chilling sections. In this manner, it is possible to install a system with solvent injection during initial cooling to a temperature greater than about 70° F., a typical hydrate initial point, without having glycol injection, and then after removal of the diamondoids using a tower, the remaining cooling can be done with glycol injection, but without the need for further solvent injection for diamondoid inhibition. Note also that in FIG. 4 and FIG. 5, the resulting rich solvent streams can be regenerated by the same regeneration system used for solvent injection upstream (near the producing well, for instance), should an upstream system be installed to protect production coolers and so on. The same injection pumps used for solvent injection into upstream equipment can also be incorporated in the injection system used for the sub-atmospheric temperature gas processing plant. The common regeneration system could be a simple blowdown/make-up arrangement, a distillation tower, or an azeotropic distillation system. Note also that the heat exchangers described as being shell and tube exchangers, with solvent and feed gas on the tube side of the exchangers could be replaced with plate-fin aluminum or stainless steel exchangers with a high number of passages, in which case industry standard means of injection of the solvent into each pass would be used.

EXAMPLE 1

This Example demonstrates the process of the present invention as described in FIG. 5 with reference to the prior art process described in FIG. 2 with regard to their ability to cool a gas stream comprising methane, nitrogen, water and diamondoids without formation of solids as preparation for any process that requires operation at sub-atmospheric temperature. The comparison is conducted under conditions such that the prior art process according to FIG. 2 adequately protects the nitrogen rejection process against water solids, but not against diamondoid solid formation or diamondoid contamination.

The feed gas composition is a natural gas containing 15% molar nitrogen and 85% molar methane at a pressure of 1000 psig and a temperature of 100° F. This gas is saturated with water and adamantine and diamantane diamondoids at these conditions. The feed gas flow rate is 10 MMscfd. At these conditions, the gas will contain approximately 60 pounds of water per 1 MMscf of gas and roughly 10 pounds total of diamondoids per 1 MMscf.

The feed gas is cooled and chilled to an operating temperature of −25° F. as preparation for absorption of the methane away from the nitrogen. Pressure drop is assumed to be negligible. At conditions of −25° F. and 1000 psig, the remaining water and remaining diamondoids in the vapor phase is less than 1 pound per 1 MMscf each. For this example, both are assumed to be 1 pound per MMscf. The amount of water that condenses and that must be held by the injected ethylene glycol solution to avoid solids is 59 lbs/MMscfd, or 590 lbs./day, or 0.41 lbs/minute. The amount of diamondoids that must be held in a solvent to avoid solids formation is 9 lbs/MMscf, or 90 lbs/day, or 0.0625 lbs/minute. It is assumed for this example that the downstream nitrogen rejection process is a solvent absorption process that uses about 750 gallons per minute of solvent circulation for the absorption, that the solvent used is octane with a density of 5 pounds/gallon, and that the solvent inventory in the system 7500 gallons.

According to the process of FIG. 2 ethylene glycol is injected, but a solvent for diamondoid inhibition or absorption is not injected. Typical lean glycol solutions used in the natural gas industry are 80% weight glycol and 20% weight water. The theoretical glycol rate is typically set as the rate required to have the rich glycol remain as at least 65% weight glycol. In this example, the lean glycol rate would be set to 1.77 lbs/minute, or with a 80% w lean glycol density at 100° F. of about 9.05 lbs/gal., about 0.2 gallons per minute. This is the theoretical rate. Actual injected rates are typically several times this theoretical rate to account for potentially poor distribution. The water that does not condense and enter the glycol solution, less than 1 pound/MMscf, will not cause problems for the nitrogen rejection system. At absorption conditions, which are essentially the same as the separator 28 conditions, no additional water will condense or freeze, the final sales gas typical specification of less than 7 pounds/MMscf of water will easily be met, and the flash regeneration will actually allow higher amounts of water to be contained in the gas. Lower pressure gas can hold more water at similar temperatures—so any water that may get entrained into the nitrogen rejection system would also not cause any freezing at the lower pressures found during flash regeneration of the circulating solvent—entrained water would enter the gas phase and leave with the sales gas.

The diamondoids are not absorbed or held in solution according to the process of FIG. 2. A suitable solvent is not added to the system to absorb the diamondoids. The 0.0625 lbs/minute of diamondoids that are condensed from the gas solidify, fouling the cooling system exchangers, becoming entrained in the glycol system sticking to the pipe walls in the glycol system, and potentially being entrained as solids into the nitrogen rejection plant. Foaming of the glycol in the glycol separator could also be caused by the diamondoid solids, leading to carry-over of glycol into the downstream solvent absorption nitrogen rejection system, and also allowing any diamondoid solids in the glycol to enter the nitrogen rejection system. The system of FIG. 2 would foul badly, and diamondoids are estimated to enter the solvent-based nitrogen rejection system at a rate of greater than the 1 lb/mmscf theoretical rate due to foaming, entrainment, and the theoretical amount of diamondoids remaining in the gas. After one year of operation at an inlet rate of 2 lb/MMscf the amount of diamondoids in the nitrogen rejection plant solvent would be 7,300 pounds, or nearly 20% of the original octane solvent inventory weight. Carryover of diamondoids into the solvent system could be very detrimental to solvent characteristics for absorption of methane, along with affecting pump and cooling loads in such a system.

Using the process of FIG. 5, the theoretical and actual practice circulation rate of lean glycol would be the same as for FIG. 2. Kerosene can be used as the solvent for the diamondoids. Although kerosene cannot dissolve as high of a concentration of diamondoids as diesel, kerosene has a lower freezing point, and can be used at −25° F. Holding capacity will be about 10% weight or volume for kerosene. If the solvent kerosene is not regenerated and is disposed of (sold) when it contains 10% diamondoids, then approximately 90 lbs/MMscf of lean (make-up pure) kerosene would need to be added to the circulating diamondoid solvent system and 100 lbs of "rich" kerosene/MMscf of gas processed would be removed from the system. This is about 150 gallons/day for a 10 MMscfd gas processing system. The actual circulation rate of kerosene to allow only a 1% change in concentration (say 9% to 10%) would be about 1 gallon per minute (6.5 lbs/minute). If the kerosene were regenerated using a tower the circulation rate could be significantly lower without risking having diamondoids condense that could not be held in solution. As the kerosene would also act as a solvent the rich kerosene would be in equilibrium with the vapor phase, and the amount of diamonds escaping into the downstream nitrogen system would be even lower than the "less than 1" pound/MMscf due to the mass transfer of the single stage of contact between the gas and the kerosene, and the very low K-value of the diamondoids.

Use of the diamondoid solvent system can significantly improve operability of a cold processing system when the gas contains diamondoids. This system can be implemented in conjunction with a dehydration system, or as a stand-alone system. It is also possible to add the diamondoid specific solvent circulation to an existing glycol injection system with minimal modifications—the major change being that the separator must accommodate separation of both the glycol and the solvent from the gas stream. It is also possible to dehydrate the gas upstream, and convert an existing glycol injection and separation system for use with a diamondoid solvent.

All of the methods and apparatus disclosed herein can be made and executed without undue experimentation in light of the present disclosure. While the methods of this invention have been described in terms of specific embodiments, it will be apparent to those of skill in the art that variations may be applied to the methods and apparatus and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended provisional claims.

What is claimed is:

1. A process for separating diamondoids from a vapor phase of a multi-component gas stream, the process comprising:
   contacting the multi-component gas stream with a lean solvent;
   cooling the gas and lean solvent mixture to less than 0° F. in one or more heat exchangers; and
   separating therefrom a diamondoid rich solvent from the vapor phase,
   wherein the vapor phase comprises less than 1 pound/MMscf diamondoids.

2. The process of claim 1, wherein the multi-component gas stream comprises methane.

3. The process of claim 1, wherein the multi-component gas stream comprises one or more components selected from the group consisting of hydrogen, nitrogen, helium, argon, methane, ethylene, ethane, heavier saturated and unsaturated hydrocarbons and mixtures thereof.

4. The process of claim 1, wherein the multi-component gas stream is contaminated with water, and ethylene glycol solvent is injected into the gas to prevent hydrate and ice formation.

5. The process of claim 4, wherein the ethylene glycol and lean solvent are mixed prior to injecting into the multi-component gas.

6. The process of claim 1, wherein the lean solvent is diesel solvent, kerosene solvent, aromatic solvent, paraffinic solvent, or naphthenic solvent.

7. The process of claim 1, wherein the multi-component gas stream is natural gas, coal gas, refinery gas, or gas from chemical plants, or other hydrocarbon containing gases.

8. The process of claim 1, wherein the lean solvent is regenerated by distilling or stripping diamondoids from the diamondoid rich solvent.

9. The process of claim 1, wherein the diamondoid rich solvent is recirculated without regeneration, and a purge/make-up arrangement is used to control diamondoid concentration in the solvent.

10. The process of claim 1, wherein the heat exchangers are shell and tube exchangers, and the multi-component gas is fed to the tube side.

11. The process of claim 10, wherein the lean solvent is injected into the mulicomponent gas stream using one or more spray nozzles located at the entrance of the heat exchanger or in the head of the exchanger.

12. The process of claim 1, wherein the heat exchangers are plate-fin exchangers, and the lean solvent is introduced into each channel of the exchanger.

13. The process of claim 1, wherein the lean solvent is the same solvent used for an upstream diamondoid removal system operating at higher temperature.

14. The process of claim 8, comprising a solvent regeneration system shared between an upstream system and the process for separating diamondoid components.

15. The process of claim 1, further comprising contacting the vapor phase with a lean solvent in a multistage absorption tower.

16. The process of claim 15, wherein the multistage absorption tower is operated at conditions below atmospheric temperature but above the coldest point of the multi-component gas stream cooling.

17. The process of claim 1, where in the gas and lean solvent mixture is cooled to less than −25° F. in one or more heat exchangers.

18. The process of claim 1, wherein the separation of the diamondoid rich solvent from the vapor phase occurs in a three-phase separator.

19. The process of claim 1, wherein the one or more heat exchanger is a plate-fin aluminum or stainless steel exchanger.

* * * * *